United States Patent [19]
Holdsworth et al.

[11] 3,932,669
[45] Jan. 13, 1976

[54] 1-CHLORO-2,2-DIMETHYL-1,4,4-TRIFLUOROCYCLOBUTANE AS AN ANESTHETICS

[75] Inventors: Robert S. Holdsworth; Gerald J. O'Neill, both of Arlington, Mass.; Paul Tarrant, Gainesville, Fla.

[73] Assignee: W. R. Grace & Co., Cambridge, Mass.

[22] Filed: Jan. 10, 1975

[21] Appl. No.: 539,958

[52] U.S. Cl. .............................................. 424/352
[51] Int. Cl.² ..................................... A61K 31/025
[58] Field of Search .................................. 424/352

[56] References Cited
UNITED STATES PATENTS

| | | | |
|---|---|---|---|
| 3,852,474 | 12/1974 | Simons et al. | 424/352 |
| 3,870,797 | 3/1975 | Holdsworth et al. | 424/352 |

*Primary Examiner*—Jerome D. Goldberg
*Attorney, Agent, or Firm*—Armand McMillan; C. E. Parker

[57] ABSTRACT

The compound 1-chloro-2,2-dimethyl-1,4,4-trifluorocyclobutane has been found to possess useful properties as a general inhalation anesthetic.

1 Claim, No Drawings

1-CHLORO-2,2-DIMETHYL-1,4,4-TRIFLUOROCYCLOBUTANE AS AN ANESTHETICS

THE PRIOR ART

Due in part to the unpredictability of the chemical and physiological behavior of organic compounds such as the halogenated alkanes and also to the lack of understanding of the mode of action of anesthetics in general, the search for new useful anesthetic agents remains beyond the scope of the routine expertise of both the chemist and the physiologist. Thus, it is, for instance, that while cyclopropane is an effective if inflammable anesthetic, one of its closely related water insoluble homologs, cyclopentane, has no medical utility. As to cyclobutanes, a recent review of the state of the art [Larsen, E. R., Fluorine Chemistry Reviews, Volume 3, page 1 (1969)] is no more enlightening in its report that of three closely related fluorocyclobutanes, one is said to possess anesthetic properties (1,2-dihydrohexafluoro-) while its more highly halogenated homologs are either toxic (1,2-dichlorohexafluoro-) or inactive (octafluoro-).

Subsequent discoveries in this field have failed to provide reliable guidelines for the identification of new useful substances from the numerous conceivable halogenated cyclobutane structures. In the case of dimethylcyclobutanes specifically, only one compound has been found to possess useful anesthetic activity. This compounds is the 1-trifluoromethyl-2-methyl-1,4,4-trifluorocyclobutane disclosed in U.S. Pat. No. 3,852,474. Other dimethylcyclobutanes tested, especially those with the two methyl groups located on the same ring carbon have been found to be deleterious.

SUMMARY OF THE INVENTION

The compound 1-chloro-2,2-dimethyl-1,4,4-trifluorocyclobutane has been found to be a useful general inhalation anesthetic.

DETAILED DESCRIPTION

The compound of this invention can be prepared by cyclizing appropriately selected ethylenic compounds in the presence of certain polymerization inhibitors. The cyclization method has been generally described by Coffman et al [J. Am. Chem. Soc. 71, 490 (1949)].

EXAMPLE 1

4-t-Butylpyrocatechol, 3.5 parts by weight, was placed in a clean stainless steel autoclave. The apparatus was sealed, checked for leaks, then cooled to approximately −75°C with dry ice in methanol. Chlorotrifluoro-ethylene, 180 parts, and isobutylene, 145 parts, were added. The autoclave was then heated at 225°C for 8 hours.

The contents of the autoclave were subsequently cooled to room temperature and transferred to a liquid nitrogen trap from which the low boiling fractions were allowed to vent slowly into a fume hood. The reaction mixture obtained was shown by gas chromatography to contain 27.2% of the theoretical quantity of product possible. Further separation and purification of the product was carried out by preparatory scale vapor chromatography to yield a material with a boiling point of 114°–5°C, a density of 1.214 at 25°C and a refractive index of 1.3827 ($n_D^{25}$).

EXAMPLE 2

The physiological effects of 1-chloro-2,2-dimethyl-1,4,4-trifluorocyclobutane were demonstrated upon mice using a standard test for evaluation of inhalation anesthetics, similar to that described by Robbins [Pharmacology and Experimental Therapeutics 86, 197 (1946)]. In this test, mice were exposed to the compound for a period of 10 minutes in a rotating drum. Observations were made of the pinch reflex, the corneal reflex and the return of the righting reflex. At least four graded doses were employed to determine the minimum concentration required to anesthetize 50% of the mice ($AC_{50}$) and the minimum concentration required to kill 50% of the mice ($LC_{50}$). The anesthetic index (AI) was then calculated from these minimum concentrations. In this manner, it was found that the cyclobutanes of this invention has an $AC_{50}$ greater than 0.5% but less than 0.75% by volume and an $LC_{50}$ of 2%, giving a anesthetic index between 2 and 3.

The compound of the invention is thus quite potent, capable of inducing a state of anesthesia in air-breathing animals, from which the latter recover, provided that the lethal concentration of anesthetic vapors is not reached.

The compound can be stored in containers of the type commonly used for commercial anesthetics of comparable boiling point, e.g. halothane, and it can be administered by means of apparatus or machines designed to vaporize liquids and mix them with air, oxygen and other gaseous combinations in quantities capable of supporting respiration. It is further contemplated that the compound herein disclosed may be used in admixture with pharmaceutially acceptable diluents and stabilizers such as thymol, or in combination with one or more of the known inhalation anesthetics.

What we claim is:

1. The process of inducing anesthesia in a mammal, which comprises administering by inhalation to said mammal an effective quantity, to induce anesthesia, of 1-chloro-2,2-dimethyl-1,4,4-trifluorocyclobutane.

* * * * *